United States Patent [19]
Hayashi et al.

[11] Patent Number: 5,151,538
[45] Date of Patent: Sep. 29, 1992

[54] ORGANOSILICON COMPOUND AND PROCESS FOR PRODUCING ORGANOSILICON COMPOUND

[75] Inventors: Teruyuki Hayashi; Toshiaki Kobayashi; Masato Tanaka, all of Tsukuba, Japan

[73] Assignee: Agency of Industrial Science and Technology, Japan

[21] Appl. No.: 464,124

[22] Filed: Jan. 12, 1990

[30] Foreign Application Priority Data

Jan. 13, 1989 [JP] Japan .................................. 1-7358
Mar. 3, 1989 [JP] Japan .................................. 1-52654

[51] Int. Cl.$^5$ ............................ C07F 7/08; C07F 7/10
[52] U.S. Cl. .................................. 556/431; 556/415; 556/419; 556/435; 546/14; 548/406; 549/214
[58] Field of Search ............... 556/435, 431, 419; 549/214; 546/14; 548/406

[56] References Cited

U.S. PATENT DOCUMENTS

| | | | |
|---|---|---|---|
| 4,788,311 | 11/1988 | Inoue | 556/435 |
| 4,861,901 | 8/1989 | Lau et al. | 556/435 X |
| 4,918,197 | 4/1990 | Rich et al. | 556/435 X |

OTHER PUBLICATIONS

C. A., 89, 214729f, 1978.
C. A., 103, 179354p, 1985.
C. A., 104, 109740h, 1986.
C. A., 89, 43566u, 1978.
C. A. Registry Handbook, 1981 Supplement, 76081-8-0-6 through 78198-83-1, #76490-69-2, A. C. S., 1981.
C. A. Registry Handbook, 1965-1971, 35-66-5 through 4599-99-9, #2889-27-2, A. C. S., 1972.
Chemical Abstracts, vol. 111, No. 19, Nov. 6, 1989 T. Kobayashi et al.
Bulletin of the Chemical Society of Japan, vol. 61, No. 7, Jul. 1988.
The Journal of Organic Chemistry, vol. 51, No. 20, 1986, issues 15-22.

Primary Examiner—Paul F. Shaver
Attorney, Agent, or Firm—Lorusso & Loud

[57] ABSTRACT

An organosilicon compound having a Si—C—C—Si bond, a C=C—Si bond and/or a CH—CH—Si bond is prepared by reacting an olefin or a substituted olefin with a disilane in the presence of a platinum-containing catalyst. The resulting compound can be further treated with an alkyl lithium, an aryl lithium or a Grignard reagent.

5 Claims, No Drawings

ORGANOSILICON COMPOUND AND PROCESS FOR PRODUCING ORGANOSILICON COMPOUND

BACKGROUND OF THE INVENTION

1. Field of the Invention

The present invention relates to novel organosilicon compounds and a process for the preparation of organosilicon compounds.

2. Description of Related Art

Alkenylsilanes may be converted into silanes having various structures by utilizing their C=C double bond as well as they may be utilized as a unique reaction of a vinyl silane for synthesis of a stereospecific olefin, an $\alpha,\beta$-unsaturated carbonyl compound as well as a stereospecific alcohol or $\alpha$-oxycarbonyl compound. They are extremely useful for intermediates for organic synthesis or for raw materials for physiologically active substances. Alkylsilanes are also useful as intermediate substances for organic synthesis and raw materials for synthesis of physiologically active substances. Their uses are disclosed in Synthesis, 1979, 761; E. W. Colvin: "Silicon in Organic Synthesis", Butterworths (1981); W. P. Weber: "Silicon Reagents for Organic Synthesis", Springer (1983), etc.

Further, bis(silyl)alkanes are used as intermediate substances for organic synthesis and for synthesis of physiologically active substances and they are polymerized into polycarbosilanes which are useful as photo-degradable polymers, resist materials having a high resistance to oxygen plasma, precursors for silicon carbide, and so on.

The alkenylsilanes are conventionally prepared as follows:

(1) by hydrosilylating an acetylene with a hydrosilane in the presence of a catalyst;

(2) by converting an acetylene into a metal acetylide and reacting the metal acetylide with a halosilane followed by reducing the resulting silyl acetylene;

(3) converting an alkenyl halide into an alkenyl metal compound which, in turn, is reacted with a halosilane;

(4) reacting an alkenyl halide with a silyl alkali metal.

The alkylsilanes may be prepared by the following conventional procedures:

(5) by hydrosilylating olefins with a hydrosilane in the presence of a catalyst; and (6) by reacting an alkali metal compound with a halosilane.

Furthermore, the bis(silyl)alkanes may be conventionally prepared as follows:

(7) by reacting a compound having an acetylenic, unsaturated bond, C≡C, with a compound having a Si—Si bond in the presence of a catalyst to thereby give a compound having a Si—C=C—Si bond which, in turn, is hydrogenated; and (8) by reacting the vinylsilane prepared in the procedures (1) to (4) above with a hydrosilane in the presence of a catalyst.

Those conventional procedures present various disadvantages and are said to be insufficient in various respects. The conventional processes as referred to as (1), (2) and (7) above use the acetylene as a raw material, which is so expensive and apt to be explosive that they accompany the difficulty in preparing on an industrial scale. The processes (1), (5) and (8) use the hydrosilane which is also expensive so that they are industrially disadvantageous. For the processes (2), (3), (4) and (6), there are used the alkali metal compounds or magnesium reagents which are also expensive as well as which may be encountered with dangers in use and which is so highly reactive that they may present the problem with protection over functional groups of the resulting compounds. Furthermore, the processes (2), (3), (4), (6), (7) and (8) are each a multi-step process which is remote from the end step.

SUMMARY OF THE INVENTION

Therefore, the present invention has the object to provide a process for the preparation of organosilicon compounds in which there are used an olefin or a substituted olefin as well as a disilane, which are easy to handle and, further, which are prepared by one step. The process according to the present invention further presents the advantage to provide novel organosilicon compounds.

Thus, the present invention has another object to provide novel organosilicon compounds.

In order to achieve the objects of the present invention, one aspect of the present invention consists of a process for preparing an organosilicon compound having a Si—C—C—Si bond and/or an organosilicon compound having a C=C—Si bond and/or an organosilicon compound having a CH—CH—Si bond by reacting an olefin compound represented by the following general formula (I):

$$R^1R^2C=CHR^3 \qquad (I)$$

wherein $R^1$, $R^2$ and $R^3$ are each hydrogen atom, an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group, and may link with each other to form a cyclic structure, with a disilane represented by the following general formula (II):

$$R^4R^5R^6Si—SiR^7R^8R^9 \qquad (II)$$

wherein $R^4$, $R^5$, $R^6$, $R^7$, $R^8$ and $R^9$ are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure, in the presence of a platinum-containing catalyst.

Another aspect of the present invention consists of process for preparing an organosilicon compound having a Si—C—C—Si bond and/or an organosilicon compound having a C=C—Si bond and/or an organosilicon compound having a CH—CH—Si bond by reacting an olefin compound represented by the following general formula (I):

$$R^1R^2C=CHR^3 \qquad (I)$$

wherein $R^1$, $R^2$ and $R^3$ are each hydrogen atom, an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group, and may link with each other to form a cyclic structure, with a disilane represented by the following general formula (II):

$$R^4R^5R^6Si\text{—}SiR^7R^8R^9 \qquad (II)$$

wherein $R^4$, $R^5$, $R^6$, $R^7$, $R^8$ and $R^9$ are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure, in the presence of a platinum-containing catalyst and thereafter by treating the resulting product with an alkyl lithium, an aryl lithium or a Grignard reagent.

A further aspect of the present invention consists of a novel compound represented by the following general formula (III):

$$A_m{}^1A_{3-m}{}^2SiCH_2CH_2SiA_n{}^3A_{3-n}{}^4 \qquad (III)$$

wherein $A^1$ and $A^3$ are each an alkyl group, and may link with each other to form a cyclic structure;

$A^2$ and $A^4$ are each an alkoxy group and an aryl group; and m and n are each 0 or an integer from 1 to 3.

A still further aspect of the present invention consists of a novel compound represented by the following general formula (IV):

$$A^5A^6A^7Si\text{—}\overset{\displaystyle\lceil\;\;A\;\;\rceil}{CH}\text{——}CH\text{—}SiA^8A^9A^{10} \qquad (IV)$$

wherein $A^5$, $A^6$, $A^7$, $A^8$, $A^9$ and $A^{10}$ are identical to or different from each other and are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure;

A is an alkylene group or a cycloalkylene group, each forming a four-membered or five-membered cycle.

Another still further aspect of the present invention consists of a novel compound represented by the following general formula (V):

$$A^5A^6A^7Si\text{—}CHA^{11}\text{—}CH_2\text{—}SiA^8A^9A^{10} \qquad (V)$$

wherein $A^5$, $A^6$, $A^7$, $A^8$, $A^9$ and $A^{10}$ are identical to or different from each other and are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure;

$A^{11}$ is an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group.

DETAILED DESCRIPTION OF THE PREFERRED EMBODIMENTS

In accordance with the process for the preparation of the organosilicon compounds of the present invention, an olefin compound is reacted with a disilane in the presence of the platinum-containing catalyst.

The olefin compound to be used as one of the starting materials is a compound of an ethylene series represented by the following general formula (I):

$$R^1R^2C=CHR^3 \qquad (I)$$

wherein $R^1$, $R^2$ and $R^3$ are each hydrogen atom, an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group, and may link with each other to form a cyclic structure.

Examples of the olefin compound include ethylene, propylene, cis-2-butene, 1-hexane, t-butylethylene, cyclopentene, norbornene, vinylcyclohexane, 2-vinyltetrahydropyrane, α-methylene-γ-butyrolactone, allylbenzene, styrene, 4-vinylpyridine, ethyl acrylate, acrylonitrile, N,N-dimethylacrylamide, methylvinyl ether, N-(1-cyclohexenyl)pyrrolidine, N-methyl-N-vinylacetamide and N-vinylphthalimide.

The disilane to be used as another starting material is a compound represented by the following formula (II):

$$R^4R^5R^6Si\text{—}SiR^7R^8R^9 \qquad (II)$$

wherein $R^4$, $R^5$, $R^6$, $R^7$, $R^8$ and $R^9$ are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure.

Illustrative of suitable disilanes are hexamethyldisilane, hexaethyldisilane, tetramethyldiphenyldisilane, tetraphenyldimethyldisilane, difluorotetramethyldisilane, dichlorotetramethyldisilane, trichlorotrimethyldisilane, tetrachlorodimethyldisilane, dimethoxytetramethyldisilane, hexachlorodisilane, tetramethoxydisilane, tetrafluorodimethyldisilane and 1,1,2,2-tetramethyl-1,2-disilacyclopentane. These compound may be used singly or in combination of one or more thereof.

The olefin compound and the disilane are used in amounts providing a molar ratio of the former to the latter ranging from approximately 100 to 1 to 1 to 10, although there is not substantial limit upon the ratio.

The platinum-containing catalyst to be used may be chosen from any known ones and may be a platinum complex with a ligand, a platinum salt or platinum supported on a carrier such as active carbon. The platinum catalyst may include, for example, tetrakis(triphenylphosphine)platinum, tetrakis(dimethylphenylphosphine)platinum, dichlorobis(triphenylphosphine)platinum, ethylenebis(triphenylphosphine)platinum, chlorohydrobis(triethylphosphine)platinum, dichloro(tetramethylethylenediamine)platinum, dibromobis(trimethylphosphine)platinum, dichlorobis(benzonitrile)platinum, bis(cyclooctadiene)platinum, dichloro(cyclooctadiene)platinum, bis(benzylideneacetone)platinum, Zeise salt, platinum chloride, chloroplatinic acid or its salt, platinum black, platinum carbon, and so on. These platinum complexes and salts may be present with a ligand.

The catalyst may be used in a stoichiometric amount and generally in an amount of 0.00001 to 0.5 mole per mole of the disilane to be used as the starting compound.

The process according to the present invention may be carried out at a temperature ranging usually from 0° C. to elevated temperatures, preferably from 50° C. to 250° C. Further, it may be carried out usually in the presence or absence of a solvent. When the solvent is used, it may include, for example, a customarily used solvent such as an organic solvent, i.e., benzene, toluene, hexane or the like.

When the disilane used as a starting material has an alkoxy group, fluorine atom, bromine atom or chlorine atom bonded to the silicon atom thereof, the organosilicon compound resulting from the above process may be further treated with an alkyl lithium, an aryl lithium or Grignard reagent, thereby yielding corresponding alkylated or arylated organosilicon compound. The alkyl lithium and the aryl lithium may preferably include methyl lithium and phenyl lithium, respectively. The Grignard reagent may include, for example, a compound represented by the following general formula:

RMgX in which reference symbol R may be any residue which varies with the group to be added or inserted into the resulting organosilicon compound and may be chosen from any per se known group, and reference symbol X may be any halogen atom which also can be chosen depending upon reactivity and other influences on the reaction system.

The resulting compound may be separated and purified in conventional manner, as by distillation or chromatography.

When ethylene is used as the olefin compound, the above processes according to the present invention, in either case, may provide an organosilicon compound represented by the following general formula (A):

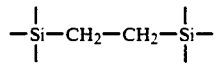   (A)

The organosilicon compounds as represented by the general formula (A) may include, for example, 1,2-bis(trimethylsilyl)ethane, 1,2-bis(triethylsilyl)ethane, 1,2-bis(dimethylphenylsilyl)ethane, 1,2-bis(methyldiphenylsilyl)ethane, 1,2-bis(fluorodimethylsilyl)ethane, 1,2-bis(chlorodimethylsilyl)ethane, 1-(chlorodimethylsilyl)-2-(dichloromethylsilyl)ethane, 1,2-bis(dichloromethylsilyl)ethane, 1,2-bis(methoxydimethylsilyl)ethane, 1,2-bis(trichlorosilyl)ethane, 1,2-bis(dimethoxymethylsilyl)ethane, 1,2-bis(difluoromethylsilyl)ethane, 1,1,4,4-tetramethyl-1,4-disilacycloheptane, or the like.

When a substituted olefin is used, the processes according to the present invention provides the organosilicon compounds represented by the following general formula (B):

$R^1R^2C=CR^3(SiR^4R^5R^6)$   (B)

wherein
$R^1$, $R^2$ and $R^3$ are each hydrogen atom, an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group, and may link with each other to form a cyclic structure; and $R^4$, $R^5$ and $R^6$ are each an alkyl group, a cycloalkyl group, an aryl group, an aralkyl group, an alkoxy group, an acyloxy group, an N,N-dialkylamino group, fluorine atom, bromine atom or chlorine atom.

Further, the processes according to the present invention can provide organosilicon compounds represented by the following general formula (C):

$R^1R^2CHCHR^3(SiR^4R^5R^6)$   (C)

wherein $R^1$, $R^2$, $R^3$, $R^4$, $R^5$ and $R^6$ have the same meanings as defined hereinabove.

Furthermore, the processes according to the present invention can provide organosilicon compounds represented by the following general formula (D):

$R^1R^2C(SiR^7R^8R^9)CHR^3(SiR^4R^5R^6)$   (D)

wherein
$R^1$, $R^2$, $R^3$, $R^4$, $R^5$ and $R^6$ have the same meanings as defined hereinabove;
$R^7$, $R^8$ and $R^9$ are each an alkyl group, a cycloalkyl group, an aryl group, an aralkyl group, an alkoxy group, an acyloxy group, an N,N-dialkylamino group, fluorine atom, bromine atom or chlorine atom, and may link with $R^4$, $R^5$ or $R^6$ to form a cyclic structure.

The organosilicon compounds represented by the general formulas (B), (C) and (D) may specifically include, for example, 1-propenylfluorodimethylsilane, 1-hexenylfluorodimethylsilane, 3,3-dimethyl-1-butenyltrimethylsilane, 2-cyclohexylvinyltrimethylsilane, 2-[2-{tri(N,N-dimethylamino)silyl}ethyl]tetrahydropyrane, α-trimethylsilylmethylidene-γ-butyrolactone, styryltrimethylsilane, 4-pyridylethenyltriethylsilane, methyl 2-(phenyldimethylsilyl)acrylate, 2-(phenyldimethylsilyl)acrylonitrile, 2-trimethylsilyl-N,N-dimethylacrylamide, propyltrimethoxysilane, n-hexylfluorodimethylsilane, 2-cyclohexylethyltrimethylsilane, 3-phenylpropyltriacetoxysilane, 3,3-dimethylbutyltrimethylsilane, methyl(2-trimethoxysilylethyl)ether, N-(2-trimethylsilyl-1-cyclohexenyl)pyrrolidine, N(2-trimethylsilylethyl)acetamide, N-(2-phenyldimethylsilylethenyl)phthalimide, 1,2-bis(trimethoxysilyl)propane, 2,3-bis(chlorodimethylsilyl)butane, 1,2-bis(chlorodimethylsilyl)cyclopentane, 2,3-bis(chlorophenylmethylsilyl)norbornane, or the like.

The novel organosilicon compound obtainable by the processes according to the present invention may be represented by the following general formula (III):

$A_m^1 A_{3-m}^2 SiCH_2CH_2SiA_n^3 A_{3-n}^4$   (III)

wherein
$A^1$ and $A^3$ are each an alkyl group, and may link with each other to form a cyclic structure;
$A^2$ and $A^4$ are each an alkoxy group and an aryl group; and
m and n are each 0 or an integer from 1 to 3.

Another type of the novel organosilicon compounds prepared by the processes according to the present invention may be represented by the following general formula (IV):

wherein
$A^5$, $A^6$, $A^7$, $A^8$, $A^9$ and $A^{10}$ are identical to or different from each other and are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure;
A is an alkylene group or a cycloalkylene group, each forming a four-membered or five-membered cycle.

A still further type of the novel organosilicon compounds prepared by the processes according to the present invention may be represented by the following general formula (V):

wherein
$A^5$, $A^6$, $A^7$, $A^8$, $A^9$ and $A^{10}$ are identical to or different from each other and are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure;
$A^{11}$ is an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group.

In the above definitions, the alkyl group and the alkoxy group and relevant terms are meant to preferably include those having from 1 to 8 carbon atoms; and the aryl group and relevant terms are meant to include particularly a phenyl group, a substituted phenyl group, and a naphthyl group and the like.

The present invention will be described in more detail by way of examples.

EXAMPLE 1

An autoclave was charged with 1 mmole of 1,1,2,2-tetramethyl-1,2-diphenyldisilane, 0.04 mmole of tetrakis(triphenylphosphine)platinum and 3 ml of benzene, and ethylene was then compressed into the autoclave at 5 atmospheric pressures. The autoclave was placed in an oil bath at 150° C. and the content was reacted for 22 hours with magnetically stirring. Thereafter, the autoclave was allowed to cool and unreacted ethylene was discharged.

The reaction mixture was analyzed by means of gas chromatography, thereby confirming the production of 0.22 mmole of 1,2-bis(dimethylphenylsilyl)ethane. The reaction mixture was then distilled under reduced pressures to give 0.13 mmole of 1,2-bis(dimethylphenylsilyl)ethane. This compound has been found to be a novel compound which is not yet published in the literature.

Its physical properties of this compound are as follows:
b.p. 90° C./0.1 torr
$^1$HNMR (CDCl$_3$): δ0.23 (s, 12H, SiCH$_3$), 0.65 (s, 4H, CH$_2$), 7.2–7.6 ppm (m, 10H, C$_6$H$_5$).
MS (70 eV): m/Z (relative intensity) 298 (M+, 7.2), 283 (17.6), 197 (10.8), 135 (100).
Elemental analysis (C$_{18}$H$_{26}$Si$_2$): Calculated: C, 72.41%; H, 8.78%. Found: C, 72.53%; H, 8.82%.

EXAMPLE 2

The procedure of Example 1 was repeated in the same manner with the exception that the reaction was carried out at 165° C. for 21 hours, thereby yielding 0.38 mmole of 1,2-bis(dimethylphenylsilyl)ethane.

EXAMPLE 3

The procedure of Example 1 was repeated in the same manner with the exception that the reaction was carried out at 170° C. using tetrakis(methyldiphenylphosphine)platinum as a catalyst, thereby yielding 0.29 mmole of 1,2-bis(dimethylphenylsilyl)ethane.

EXAMPLE 4

The procedure of Example 3 was repeated in the same manner with the exception that the reaction was carried out at 200° C., thereby yielding 0.60 mmole of 1,2-bis(dimethylphenylsilyl)ethane.

EXAMPLE 5

The procedure of Example 1 was repeated in the same manner with the exception that the reaction was carried out using 1 mmole of 1,2-dimethoxy-1,1,2,2-tetramethyldisilane in place of 1,1,2,2-tetramethyl-1,2-diphenyldisilane, thereby yielding 0.63 mmole of 1,2-bis(dimethoxydimethylsilyl)ethane by distillation of the reaction mixture.

This compound is a novel compound and has the following physical properties:
b.p. 70° C./12 torr
$^1$HNMR (CDCl$_3$): δ0.02 (s, 12H, SiCH$_3$), 0.45 (s, 4H, CH$_2$), 3.33 (s, 6H, OCH$_3$).
MS (70 eV): m/Z (relative intensity) 206 (M+, 1.5), 191 (22.9), 163 (21.5), 105 (15.4), 89 (100), 59 (56.1).
Elemental analysis (C$_8$H$_{22}$Si$_2$): Calculated: C, 46.55%; H, 10.74%. Found: C, 46.63%; H, 10.79%.

EXAMPLE 6

The procedure of Example 1 was repeated in the same manner with the exception that the reaction was carried out using 1 mmole of 1,2-difluoro-1,1,2,2-tetramethyldisilane in place of 1,1,2,2-tetramethyl-1,2-diphenyldisilane, thereby yielding 0.93 mmole of 1,2-bis(fluorodimethylsilyl)ethane.

EXAMPLE 7

The procedure of Example 1 was repeated in the same manner with the exception that the reaction was carried out using 1 mmole of a mixture of 1,1,2-trichloro-1,2,2-trimethyldisilane and 1,1,2,2-tetrachloro-1,2-dimethyldisilane (3:7) in place of 1,1,2,2-tetramethyl-1,2-diphenyldisilane, thereby yielding 0.69 mmole of a mixture of 1-(chlorodimethylsilyl)-2-(dichloromethylsilyl)ethane and 1,2-bis(dichloromethylsilyl)ethane (4:6).

EXAMPLE 8

The procedure of Example 1 was repeated in the same manner with the exception that the reaction was carried out using 1 mmole of hexamethyldisilane in place of 1,1,2,2-tetramethyl-1,2-diphenyldisilane, thereby yielding 0.18 mmole of 1,2-bis(trimethylsilyl)ethane.

EXAMPLE 9

The procedure of Example 1 was repeated in the same manner with the exception that the reaction was carried out using 1 mmole of 1,2-dichloro-1,1,2,2-tetramethyldisilane in place of 1,1,2,2-tetramethyl-1,2-diphenyldisilane, thereby yielding 0.60 mmole of 1,2-bis(chlorodimethylsilyl)ethane.

EXAMPLE 10

The procedure of Example 1 was repeated in the same manner with the exception that the reaction was carried out using 0.04 mmole of tetrakis(triethylphosphine)platinum in place of tetrakis(triphenylphosphine)platinum, thereby yielding 0.12 mmole of 1,2-bis(dimethylphenylsilyl)ethane, 0.10 mmole of dimethylphenylvinylsilane, and 0.10 mmole of ethyldimethylphenylsilane.

EXAMPLE 11

The procedure of Example 1 was repeated in the same manner with the exception that the reaction was carried out using 0.04 mmole of tetrakis(dimethylphosphine)platinum in place of tetrakis(dimethylphenylphosphine)platinum, thereby yielding 0.30 mmole of 1,2-bis(dimethylphenylsilyl)ethane, 0.21 mmole of dimethylphenylvinylsilane, and 0.16 mmole of ethyldimethylphenylsilane.

EXAMPLE 12

The procedure of Example 1 was repeated in the same manner with the exception that the reaction was carried out using 0.04 mmole of tetrakis(trimethylphosphine)platinum in place of tetrakis(triphenylphosphine)platinum, thereby yielding 0.33 mmole of 1,2-bis(dimethylphenylsilyl)ethane, 0.67 mmole of dimethylphenylvinylsilane, and 0.65 mmole of ethyldimethylphenylsilane.

EXAMPLE 13

The procedure of Example 1 was repeated in the same manner with the exception that the reaction was carried out using 0.04 mmole of ethylenebis(triphenylphosphine)platinum in place of tetrakis(triphenylphosphine)platinum, thereby yielding 0.03 mmole of 1,2-bis(dimethylphenylsilyl)ethane.

EXAMPLE 14

The procedure of Example 1 was repeated in the same manner with the exception that the reaction was carried out using 1 mmole of 1,1,2,2-tetramethyl-1,2-bis(p-trifluoromethylphenyl)disilane in place of 1,1,2,2-tetramethyl-1,2-diphenyldisilane, thereby yielding 0.16 mmole of 1,2-bis[dimethyl(p-trifluoromethylphenyl)silyl]ethane. This compound is a novel compound.
m.p. 58°–59° C.
$^1$HNMR (CDCl$_3$): δ0.20 (s, 12H, SiCH$_3$), 0.58 (s, 4H, CH$_2$CH$_2$), 7.51 (s, 8H, C$_6$H$_4$).
MS (70 eV): m/Z (relative intensity) 434 (M+, 6), 419 (13), 415 (8), 333 (4), 329 (2), 203 (100), 184 (55).

Elemental analysis (C$_8$H$_{22}$Si$_2$): Calculated: C, 55.28%; H, 5.57%. Found: C, 55.04%; H, 5.58%.

EXAMPLE 15

The procedure of Example 1 was repeated in the same manner with the exception that the reaction was carried out using 1 mmole of 1,1,2,2-tetramethyl-1,2-bis(p-tolyl)disilane in place of 1,1,2,2-tetramethyl-1,2-diphenyldisilane, thereby yielding 0.04 mmole of 1,2-bis[dimethyl(p-tolyl)silyl]ethane. This compound is a novel compound.
MS (70 eV): m/Z (relative intensity) 326 (M+, 5), 312 (6), 311 (19), 225 (10), 162 (11), 150 (16), 149 (100).

EXAMPLE 16

The procedure of Example 6 was repeated in the same manner with the exception that the reaction was carried out at 100° C., thereby yielding 0.98 mmole of 1,2-bis(fluorodimethylsilyl)ethane.

EXAMPLE 17

The procedure of Example 6 was repeated in the same manner with the exception that 8.9 mmole of 1,2-difluoro-1,1,2,2-tetramethyldisilane was used without a solvent, ethylene was charged at the pressure of 50 atmospheric pressures, and the reaction time was 18 hours, thereby distilling and yielding 6.0 mmole of 1,2-bis(fluorodimethylsilyl)ethane.

EXAMPLE 18

The procedure of Example 9 was repeated in the same manner with the exception that the reaction was carried out at 120° C., thereby yielding 0.87 mmole of 1,2-bis(chlorodimethylsilyl)ethane.

EXAMPLE 19

The procedure of Example 9 was repeated in the same manner with the exception that the reaction was carried out at 100° C., thereby yielding 0.79 mmole of 1,2-bis(chlorodimethylsilyl)ethane.

EXAMPLE 20

The procedure of Example 16 was repeated in the same manner with the exception that a flask equipped with a balloon of an atmospheric pressure of ethylene was used in place of the autoclave.
The resulting mixture was stirred with a 0.6M etheric solution of phenyllithium for 2 hours, thereby yielding 0.74 mmole of 1,2-bis(dimethylphenylsilyl)ethane.

EXAMPLE 21

A pressure reactor was charged with 1 mmole of 1,2-difluorotetramethyldisilane, 5 mmole of styrene, 0.04 mmole of tetrakis(triphenylphosphine)platinum, and 3 ml of benzene, and the reactor was placed in an oil bath at 150° C. The content was stirred magnetically for 22 hours. After the reactor was allowed to cool, it was opened. The reaction mixture was then analyzed by means of gas chromatography, thereby confirming the formation of β-E-(fluorodimethylsilyl)styrene, β-Z-(fluorodimethylsilyl)styrene, β-(fluorodimethylsilyl)ethylbenzene, α,β-bis(fluorodimethylsilyl)ethylbenzene. α,β-Bis(fluorodimethylsilyl)ethylbenzene is a novel compound.
MS (EI): m/Z (relative intensity) 258 (M+, 4), 181 (11), 165 (5), 162 (25), 147 (36), 139 (4), 135 (6), 77 (100), 49 (14), 47 (10).

The resulting reaction mixture was treated with a 0.6M etheric solution of phenyl lithium for 2 hours, thereby yielding 0.80 mmole of β-E-(dimethylphenylsilyl)styrene, 0.11 mmole of β-Z-(dimethylphenylsilyl)styrene, 0.10 mmole of β-(dimethylphenylsilyl)ethylbenzene, and 0.04 mmole of α, β-bis(dimethylphenylsilyl)ethylbenzene. α, β-Bis(dimethylphenylsilyl)ethylbenzene is a novel compound.

MS (EI): m/Z (relative intensity) 374 (M+, 2), 224 (11), 209 (3), 197 (5), 162 (26), 147 (4), 146 (5), 135 (100), 107 (5), 105 (6), 43 (9).

EXAMPLE 22

The procedure has been followed in the same manner as in Example 21 with the exception that 1-hexane was used in place of styrene and thereafter the resulting mixture was stirred with a 0.6M etheric solution of phenyl lithium for 2 hours, thereby yielding 0.55 mmole of 1-(dimethylphenylsilyl)-1-hexene, 0.38 mmole of 1-E-(dimethylphenylsilyl)-1-hexene, 0.18 mmole of 1-Z-(dimethylphenylsilyl)-1-hexene, and 0.09 mmole of 1,2-bis(dimethylphenylsilyl)hexene. 1,2-Bis(dimethylphenylsilyl)hexene is a novel compound.

MS (EI): m/Z (relative intensity) 339 (M−15+, 21), 276 (9), 203 (14), 197 (21), 189 (9), 135 (100), 121 (18), 114 (11).

EXAMPLE 23

The procedure has been followed in the same manner as in Example 21 with the exception that the reaction was carried out at 100° C., and then the product was treated with phenyl lithium in the same manner, thereby yielding 0.48 mmole of β-E-(dimethylphenylsilyl)styrene, 0.3 mmole of β-Z-(dimethylphenylsilyl)styrene, 0.15 mmole of β-(dimethylphenylsilyl)ethylbenzene, and 0.04 mmole of α, β-bis(dimethylphenylsilyl)ethylbenzene.

EXAMPLE 24

The procedure has been followed in the same manner as in Example 21 with the exception that norbornene was used in place of styrene, thereby yielding 0.26 mmole of 2-exo-3-exo-bis(fluorodimethylsilyl)norbornane. This compound is a novel compound.

MS (EI): m/Z (relative intensity) 233 (M−15+, 5), 171 (6), 152 (25), 137 (7), 124 (61), 109 (23), 105 (13), 93 (13), 77 (100).

This compound was then treated with methyl lithium, thereby yielding 0.19 mmole of 2-exo-3-exo-bis(trimethylsilyl)norbornane. This compound, too, is a novel compound.

b.p. 80°-90° C./28 mm

High-Resolving Power MS: M+240.1736 Calculated (as $C_{13}H_{28}Si_2$): 240.1729.

MS (EI): m/Z (relative intensity) 240 (M+, 2), 167 (11), 151 (3), 131 (6), 124 (5), 109 (3), 101 (2), 73 (100).

$^1$H-NMR (200 MHz, $C_6D_6$): δ0.14 (s, 18H, SiCH$_3$) 0.89 (d, J=1.7 Hz, 2H, SiCH) 1.05–1.38 (m, 4H, methylene CH$_2$, ethylene CH (endo)) 1.61–1.73 (m, 2H, ethylene CH(exo)) 2.25–2.33 (m, 2H, bridge head CH) ppm $^{13}$CNMR ($C_6D_6$): δ0.5 (SiCH$_3$), 34.3, 36.0, 38.4, 40.1 (norbornane) ppm.

EXAMPLE 25

The procedure has been followed in the same manner as in Example 21 with the exception that cyclopentene was used, thereby yielding 0.19 mmole of 1,2-bis(fluorodimethylsilyl)cyclopentane. This compound is a novel compound.

MS (EI): m/Z (relative intensity) 207 (M−15+, 5), 144 (2), 129 (13), 126 (28), 118 (11), 111 (11), 98 (13), 85 (23), 77 (100), 66 (93), 59 (36), 49 (21), 47 (14).

EXAMPLE 26

The procedure has been followed in the same manner as in Example 21 with the exception that ethyl acrylate was used in place of styrene, thereby yielding 0.33 mmole of ethyl fluorodimethylsilylacrylate and 0.19 mmole of ethyl fluorodimethylsilylpropionate.

EXAMPLE 27

The procedure has been followed in the same manner as in Example 21 with the exception that acrylonitrile was used in place of styrene, thereby yielding 0.19 mmole of fluorodimethylsilylacrylonitrile.

EXAMPLE 28

The procedure has been followed in the same manner as in Example 21 with the exception that propylene was used in place of styrene, thereby yielding 0.04 mmole of trans-1-propenylfluorodimethylsilane, 0.06 mmole of propylfluorodimethylsilane, and 0.06 mmole of 1,2-bis(fluorodimethylsilyl)propane.

The novel organosilicon compound of the general formula (IV), such as a bis(chlorodialkylsilyl)norbornane or a bis(chlorodialkylsilyl)cyclopentane, may be suitably used as a precursor for the formation of an elastic polymer having a plurality of the following recurring units:

What is claimed is:

1. A process for preparing an organosilicon compound having a Si—C—C—Si bond, a C=C—Si bond and/or a CH—CH—Si bond, comprising the step of (a) reacting an olefin compound represented by the following general formula (I):

$$R^1R^2C=CHR^3 \qquad (I)$$

wherein $R^1$, $R^2$ and $R^3$ are each hydrogen atom, an alkyl group, a cycloalkyl group, an aliphatic heterocyclic group, an aralkyl group, an aryl group, an aromatic heterocyclic group, an alkoxycarbonyl group, a cyano group, an N,N-dialkylaminocarbonyl group, an alkoxy group, an N,N-dialkylamino group, an N-alkyl-N-acylamino group or an N,N-diacylamino group, and may link with each other to form a cyclic structure, with a disilane represented by the following general formula (II):

$$R^4R^5R^6Si-SiR^7R^8R^9 \qquad (II)$$

wherein $R^4$, $R^5$, $R^6$, $R^7$, $R^8$ and $R^9$ are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure, in the presence of a platinum-containing catalyst.

2. A process as claimed in claim 1, wherein the olefin compound and the disilane are used in amounts providing a molar ratio of the former to the latter ranging from 100:1 to 1:10.

3. A process as claimed in claim 1, wherein the platinum-containing catalyst is used in an amount ranging from 0.00001 to 0.5 in mole with respect to the disilane used.

4. A process as claimed in claim 1, further comprising the step of (b) treating the product obtained in step (a) with an alkyl lithium, an aryl lithium or Grignard reagent.

5. A novel compound as represented by the following general formula (IV):

$$A^5A^6A^7Si-\overset{\displaystyle\lceil\ A\ \rceil}{CH}\text{------}CH-SiA^8A^9A^{10} \qquad (IV)$$

wherein $A^5$, $A^6$, $A^7$, $A^8$, $A^9$ and $A^{10}$ are identical to or different from each other and are each an alkyl group, a cycloalkyl group, an aryl group, an aralkyl group, an alkoxy group, an acyloxy group, an N,N-dialkylamino group, fluorine atom, bromine atom or chlorine atom, and may link with each other to form a cyclic structure; A is an alkylene group or a cycloalkylene group, each forming a four-membered or five-membered ring.

* * * * *